(12) United States Patent
Kleen et al.

(10) Patent No.: US 9,693,937 B2
(45) Date of Patent: Jul. 4, 2017

(54) FOIL APPLICATOR

(71) Applicant: Henkel AG & Co. KGaA, Dusseldorf (DE)

(72) Inventors: Astrid Kleen, Hamburg (DE); Susanne Hagenow, Hamburg (DE); Carolin Welz, Hamburg (DE)

(73) Assignee: HENKEL AG & CO. KGAA, Dusseldorf (DE)

( * ) Notice: Subject to any disclaimer, the term of this patent is extended or adjusted under 35 U.S.C. 154(b) by 0 days.

(21) Appl. No.: 14/635,305

(22) Filed: Mar. 2, 2015

(65) Prior Publication Data

US 2015/0174019 A1 Jun. 25, 2015

Related U.S. Application Data

(60) Division of application No. 13/290,487, filed on Nov. 7, 2011, now abandoned, which is a continuation of application No. PCT/EP2010/053660, filed on Mar. 22, 2010.

(30) Foreign Application Priority Data

May 7, 2009 (DE) ........................ 10 2009 002 908

(51) Int. Cl.
| | |
|---|---|
| *A61Q 5/08* | (2006.01) |
| *A61K 8/22* | (2006.01) |
| *A45D 19/00* | (2006.01) |
| *A61K 8/02* | (2006.01) |
| *A61K 8/42* | (2006.01) |
| *A61K 8/49* | (2006.01) |
| *A61K 8/81* | (2006.01) |
| *A61K 8/23* | (2006.01) |

(52) U.S. Cl.
CPC ............ *A61K 8/22* (2013.01); *A45D 19/0025* (2013.01); *A61K 8/02* (2013.01); *A61K 8/0204* (2013.01); *A61K 8/0216* (2013.01); *A61K 8/23* (2013.01); *A61K 8/42* (2013.01); *A61K 8/4966* (2013.01); *A61K 8/8176* (2013.01); *A61Q 5/08* (2013.01); *A45D 2019/0066* (2013.01); *A45D 2019/0091* (2013.01); *A61K 2800/31* (2013.01); *A61K 2800/87* (2013.01)

(58) Field of Classification Search
None
See application file for complete search history.

(56) References Cited

U.S. PATENT DOCUMENTS

| | | |
|---|---|---|
| 5,931,168 A | 8/1999 | Abercrombie et al. |
| 2003/0077237 A1 | 4/2003 | Legrand et al. |
| 2003/0135937 A1 | 7/2003 | Barass et al. |
| 2003/0143167 A1 | 7/2003 | Kleen |

FOREIGN PATENT DOCUMENTS

| | | |
|---|---|---|
| DE | 19543989 A1 | 5/1997 |
| DE | 102006008542 A1 | 12/2006 |
| EP | 1792641 A2 | 6/2007 |
| EP | 1958532 A2 | 8/2008 |
| WO | 9310687 A1 | 6/1993 |

*Primary Examiner* — Jyothsna Venkat
(74) *Attorney, Agent, or Firm* — Lorenz & Kopf, LLP

(57) ABSTRACT

Foil-type applicator for the selective lightening of keratin fibers, particularly human hair, and use of the applicators for producing targeted lightening effects on the hair.

5 Claims, No Drawings

FOIL APPLICATOR

CROSS REFERENCE TO RELATED APPLICATIONS

This application is a divisional application of U.S. patent application Ser. No. 13/290,487 filed Nov. 7, 2011, which is a continuation of International Patent Application No. PCT/EP2010/053660 filed 22 Mar. 2010, which claims priority to German Patent Application No. 10 2009 002 908.7 filed 7 May 2009, all of which are incorporated herein by reference.

The present invention relates to a foil-like applicator for, in particular, selective lightening of the color of keratinic fibers, particularly human hair, and the use of such applicators to generate targeted lightening effects in hair.

The natural color and shine or gloss of hair are lost or modified over time, particularly in response to external influences such as light or atmospheric pollutants. Lightening of hair is a particular focus of users. Lightening agents, found either in salons or for home application, are widely used for this reason. Several problems occur in coloring hair, especially coloring hair at home. On the one hand, natural color shades are completely covered, so that multi-tone color results are difficult to implement. On the other hand, selective lightening of individual portions of hair, for example, fiber bundles, strands, and partings, is difficult to achieve without suitable aids. The utilization of suitable aids such as applicators or brushes often, however, demands a great deal of experience and skill.

In order to impart a natural appearance to the hair, it is proposed to partially decolorize uncolored or colored hair by targeted application of oxidizing agents. The hair portions ("highlights") onto which the oxidizing agents are applied become bleached out at least in part, resulting in a multi-tone hair color. The oxidizing agent is applied using a brush or paintbrush, the hair to be treated being, if applicable, selected using aluminum foil or a "highlight cap".

The existing art, particularly WO 1993/010687 A1, has therefore proposed the use of highlight foils or highlight papers for creating highlights. These are flexible substrates that are impregnated with an activator or lightening agent. The impregnated substrates are treated before use with an oxidizing agent in order to create the actual lightening preparation, applied by wrapping them around the strands to be lightened.

Mixing on the foil presents some disadvantages for the user. On the one hand it is necessary to ensure that all the foils are treated with the same quantity of oxidizing agent. On the other hand, once the oxidizing agent preparation has been mixed in, the time in which application onto the strand can occur is limited. Different preparation compositions and/or varying application time periods can result in undesired and non-uniform lightening results. A demand, therefore, still exists for applicator forms that can be utilized easily by inexperienced users in particular, for selective lightening of portions of hair, particularly for generating highlights.

It has now been found that a special applicator in foil form can advantageously be used for targeted and selective application of lightening agents if the applicator is a foil coated with a lightening agent that is wrapped around wet hair, wherein the lightening agent becomes active on the hair as a result of the moisture of the hair.

This form of foil applicator advantageously differs from the existing art in that complex, time-intensive pre-mixing of the agent on the foil is eliminated. Problems that may occur with quantitative ratios between activator and oxidizing agent, or with homogenization of the agent, are likewise avoided. In addition, the application time for the hair-bleaching agent can be precisely adhered to with applicators according to the present invention, since the lightening operation begins only upon contact of the foil applicator with the hair or hair strands. The user can thus accurately determine the contact time of the lightening agent.

Lastly, the user can very precisely define the lightening location in the hair by selecting a strand, and can apply the lightening agent specifically at the desired location of action, which is possible only insufficiently in the context of application with a brush or paintbrush.

A first subject of the present invention is therefore a foil applicator for selective lightening of keratinic fibers, encompassing a sheet-shaped substrate as well as a cosmetic hair-bleaching preparation applied onto the substrate, wherein the hair-bleaching preparation is anhydrous and contains at least one solid peroxodisulfate salt as well as at least one solid addition product of hydrogen peroxide with organic or inorganic compounds.

The terms "foil applicator," "highlight foil," respectively "applicator", are used synonymously hereinafter.

The applicator according to the present invention comprises a flexible substrate. The flexible substrate can assume any shape and can be made of any material or any material mixture that is flexible. "Flexible" for purposes of the present invention refers to substrates that, in terms of shape and materials, can be deformed with manual force, with a reversible deformation being preferred. Flexible substrates according to the present invention are sheet-shaped. "Sheet-shaped" means, for purposes of the present invention, that the physical extension of the substrate along one spatial direction is considerably smaller than along the other two spatial directions. The smallest physical extension of the substrate being referred to in the context of the present invention as "height", while the corresponding extensions of the substrate in the spatial directions orthogonal thereto are referred to as "width" and "length." If the physical extension of the substrate along the spatial directions running orthogonally to the height is different, then in the context of the present invention the smaller physical extension is referred to as "width" and the larger as "length".

In preferred substrates according to the present invention, the ratio of width to height is 10 to 1 to 100,000 to 1, preferably 50 to 1 to 50,000 to 1, and particularly 100 to 1 to 1000 to 1. Particularly preferred sheet-shaped substrates according to the present invention have a height equal to 10 to 1000 µm, preferably 25 to 500 µm, and particularly 40 to 250 µm. The length and width of preferred sheet-shaped substrates are preferably from 1 to 30 cm, more preferably from 2 to 20 cm, even more preferably from 3 to 15 cm, and particularly from 4 to 12 cm.

A preferred embodiment of the foil applicator is characterized in that the sheet-shaped substrate has a thickness from 5 µm to 10 mm, preferably from 10 µm to 1 mm, more preferably from 15 µm to 0.5 mm, and particularly from 20 µm to 0.1 mm.

In the interest of stable shaping in the context of the lightening process, and in consideration of the fact that the sheet-shaped substrate is to be left resting in stable fashion around a hair strand without further mechanical aids, the use of aluminum foils is particularly preferred. Because aluminum foil is not chemically stable to a large degree with respect to the ready-to-apply hair-bleaching composition, multi-layer sheet-shaped substrates are recommended such as double-ply foils of plastic and aluminum. Laminates in which the individual layers are adhesively bonded to one another are particularly suitable for this.

Preferred foil applicators according to the present invention are those wherein the sheet-shaped substrate comprises at least one layer made of aluminum foil.

Sheet-shaped substrates according to the present invention can be made of different materials or material mixtures, with paper, paperboard, and foils having proven successful.

Paper is a planar material made substantially from fibers typically of vegetable origin, that is formed by dewatering a slurry of fibrous material on a sieve. This produces a fiber felt that is then compressed and dried. The weight of paper is usually less than or equal to 225 g/m². Paperboard is a planar material made substantially from fibers usually of vegetable origin that in terms of basis weight (150 to 600 g/m²) includes both papers and corrugated boards. It is stiffer than paper and is generally manufactured from higher-grade materials than corrugated board. Paperboard is produced as an endless web. Foils (from Latin "folium"=leaf) are thin, planar, flexible, coilable webs of made of metals (e.g., gold leaf, aluminum tin foil) or plastics (e.g., cellulose acetate, PVC, polyethylene, etc.). Particularly thin foils are also called "films." Metal foils are obtained by rolling or beating, plastic films by casting, calendering, or extrusion, which is carried out by blow-molding, resulting in tubular or blown films that are then cut.

Foil materials particularly suitable according to the present invention are plastics, with thermoplastics having proven particularly successful. "Plastics" are generally understood as materials whose essential constituents are made of macromolecular organic compounds produced synthetically or by modifying natural products. In many cases they can be melted and shaped under certain conditions (e.g., heat and pressure). Plastics can generally be manufactured in accordance with all poly-type (polyaddition, polycondensation, and polymerization processes) and polymer-analogous reactions usual for the synthesis of polymers. Sheet-shaped substrates particularly preferred according to the present invention are manufactured from one or more of the following plastics: Cellulose nitrate, cellulose acetate, cellulose mixed esters, cellulose ethers, polyamide, polycarbonate, polyester, polyvinylacetal, polyethylene, polypropylene, poly-1-butene, polybutadiene, polyisoprene, poly-4-methyl-1-pentene, ionomers, polyvinyl chloride polyvinylidene chloride, polymethyl methacrylate, polyacrylonitrile, polystyrene, polyacetal, fluorine plastics, polyvinyl alcohol, polyvinyl acetate, linear polyurethanes, and chlorinated polyethers.

The anhydrous hair-bleaching preparation that is applied onto the sheet-shaped substrate can be present in solid, semi-solid, liquid, dispersed, emulsified, suspended, or gelled form. In one embodiment, the hair-bleaching preparation is present in solid form.

"Anhydrous" means, for purposes of the invention, that the hair-bleaching preparation possesses a water content of less than 5.0 wt %, preferably less than 1.0 wt %, particularly less than 0.1 wt %, and very particularly preferably less than 0.05 wt %, based on total weight of the hair-bleaching preparation.

Full-coverage coating of the sheet-shaped substrate can exist or only specific areas of the substrate can be coated. The quantity and layer thickness of the preparation can also vary depending on the desired manner of application. The masses of the substrate and preparation are preferably coordinated with one another. Highlight foils according to the present invention in which the hair-bleaching preparation accounts for at least 10 wt %, preferably at least 25 wt %, and particularly at least 50 wt % of the total weight of the highlight foil are preferred here.

The hair-bleaching preparation for coating the foil contains at least one solid addition product of hydrogen peroxide with organic or inorganic compounds, and at least one solid peroxodisulfate salt.

Hydrogen peroxide can form addition products with many inorganic and organic compounds. These include addition products with urea (urea-hydrogen peroxide addition compound, UHP, Hydroperite, perhydrol-urea, hydrogen peroxide carbamide, percarbamide), melamine (melamine peroxide), and polyvinyl pyrrolidinone ($PVP.nH_2O_2$), as well as percarbonates, particularly sodium percarbonate and magnesium percarbonate, and perborates, particularly sodium perborate.

In a preferred embodiment, the hair-bleaching preparation contains a solid addition product of hydrogen peroxide with organic or inorganic compounds chosen from addition products with urea, melamine and polyvinyl pyrrolidinone.

The hair-bleaching preparations contain the solid addition product of hydrogen peroxide with organic or inorganic compounds in a quantity from 0.1 to 60 wt %, preferably from 1 to 50 wt %, and particularly preferably from 2 to 30 wt %, calculated in each case as 100% $H_2O_2$ and based on total weight of the hair-bleaching preparation.

As a further essential ingredient, the hair-bleaching preparations contain at least one solid peroxodisulfate salt for activating and intensifying the lightening effect of the preparation.

In one embodiment of the present invention the solid peroxodisulfate salt is chosen from ammonium peroxodisulfate, potassium peroxodisulfate, and sodium peroxodisulfate.

It is further particularly preferred, in the context of the present invention, if agents according to the invention contain at least two different peroxodisulfates. Preferred peroxodisulfate salts are combinations of ammonium peroxodisulfate and potassium peroxodisulfate and/or sodium peroxodisulfate.

The hair-bleaching preparations contain solid peroxodisulfate salts in a quantity from 0.1 to 40 wt %, preferably from 1 to 30 wt %, and particularly preferably from 2 to 20 wt %, based on total weight of the hair-bleaching preparation.

Hair-bleaching preparations according to the present invention can contain a further bleaching power intensifier in addition to the solid peroxodisulfate salts.

Suitable bleaching power intensifiers include inorganic peroxo compounds chosen from ammonium peroxomonosulfate, alkali-metal peroxomonosulfates, alkali-metal peroxodiphosphates, and alkaline-earth metal peroxides. Particularly preferred bleaching power intensifiers are potassium hydrogenperoxomonosulfate, potassium peroxodiphosphate, magnesium peroxide, and barium peroxide.

Compounds that, under perhydrolysis conditions, yield aliphatic peroxocarboxylic acids preferably having 1 to 10 carbon atoms, particularly 2 to 4 carbon atoms, and/or optionally substituted perbenzoic acid can likewise be used as bleach intensifiers. Multiply acylated alkylenediamines, in particular tetraacetylethylenediamine (TAED), acylated triazine derivatives, particularly 1,5-diacetyl-2,4-dioxohexahydro-1,3,5-triazine (DADHT), acylated glycolurils, particularly tetraacetyl glycoluril (TAGU), N-acylimides, particularly N-nonanoyl succinimide (NOSI), acylated phenolsulfonates, particularly n-nonanoyl or isononanoyl oxybenzenesulfonate (n- or iso-NOBS), carboxylic acid anhydrides, particularly phthalic acid anhydride, acylated polyvalent alcohols, particularly triacetin, ethylene glycol diacetate, and 2,5-diacetoxy-2,5-dihydrofuran are preferred.

In preferred fashion, carbonate salts, respectively hydrogencarbonate salts, can be used as bleach intensifiers of the carbonic-acid derivative type. These are preferably chosen from ammonium, alkali-metal (particularly potassium and sodium), and alkaline-earth metal (particularly magnesium and calcium) carbonate salts, respectively hydrogencarbonate salts. Particularly preferred carbonate salts are ammonium hydrogencarbonate, ammonium carbonate, sodium hydrogencarbonate, sodium carbonate, potassium hydrogencarbonate, potassium carbonate, magnesium carbonate, and calcium carbonate. These particularly preferred salts can be used as bleach intensifiers alone or in mixtures of at least two representatives thereof.

Alkyl carbonates, alkyl carbamates, silyl carbonates, and silyl carbamates are other bleach intensifiers suitable according to the present invention.

Further bleaching power intensifiers usable according to the present invention can be made of nitrogen-containing, optionally cationic heterocycles. Imidazole is an example of a nitrogen-containing heterocyclic bleaching power intensifier.

Nitrogen-containing heterocyclic bleaching power intensifiers are preferably chosen from cationic heterocycles. Among these, cationic pyridines, pyrimidines, pyrazines, pyridazines, triazines, imidazoles, thiazoles, oxazoles, isoxazoles, quinolines, isoquinolines, and partially or completely saturated analogs thereof are particularly preferred.

Particularly preferred nitrogen-containing heterocyclic bleaching power intensifiers are the quaternized cations of pyridines and of 3,4-dihydroisoquinolines.

Preferred bleaching power intensifiers of the pyridinium salt type include 4-acetyl-1-methylpyridinium-p-toluenesulfonate, 4-acetyl-1-methylpyridiniumbenzenesulfonate, 4-acetyl-1-methylpyridinium bromide, 4-acetyl-1-methyl-pyridinium hydrogen sulfate, 4-acetyl1-allylpyridinium-p-toluenesulfonate, 4-acetyl-1-allylpyridiniumbenzenesulfonate, 4-acetyl-1-allylpyridinium bromide, 4-acetyl-1-allylpyridinium hydrogen sulfate, 4-acetyl-1-(2-hydroxyethyl)pyridinium-p-toluenesulfonate, 4-acetyl-1-(2-hydroxyethyl)pyridiniumbenzenesulfonate, 4-acetyl-1-(2-hydroxyethyl)pyridinium bromide, 4-acetyl-1-(2-hydroxyethyl)pyridinium hydrogen sulfate, 4-acetyl-1-(2-oxopropyl)pyridinium-p-toluenesulfonate, 4-acetyl-1-(2-oxopropyl)pyridiniumbenzenesulfonate, 4-acetyl-1-(2-oxopropyl)pyridinium bromide, 4-acetyl-1-(2-oxopropyl)pyridinium hydrogen sulfate, 4-acetyl-1-ethylpyridinium-p-toluenesulfonate, 4-acetyl-1-ethylpyridiniumbenzenesulfonate, 4-acetyl-1-ethylpyridinium bromide, 4-acetyl-1-ethyl-pyridinium hydrogen sulfate, 4-acetyl-1-(2-methylprop-2-enyl)pyridinium-p-toluenesulfonate, 4-acetyl-1-(2-methylprop-2-enyl)pyridiniumbenzenesulfonate, 4-acetyl-1-(2-methylprop-2-enyl)pyridinium bromide, 4-acetyl-1-(2-methylprop-2-enyl)pyridinium hydrogen sulfate, 4-acetyl-1-benzylpyridinium-p-toluenesulfonate, 4-acetyl-1-benzyl-pyridiniumbenzenesulfonate, 4-acetyl-1-benzylpyridinium bromide, 4-acetyl-1-benzylpyridinium hydrogen sulfate, 4-acetyl-1-(2-methoxyethyl)pyridinium-p-toluenesulfonate, 4-acetyl-1-(2-methoxyethyl)pyridiniumbenzenesulfonate, 4-acetyl-1-(2-methoxyethyl)pyridinium bromide, or 4-acetyl-1-(2-methoxyethyl)pyridinium hydrogen sulfate, as well as 2-acetyl-1-methylpyridinium-p-toluenesulfonate, 2-acetyl-1-methylpyridiniumbenzenesulfonate, 2-acetyl-1-methylpyridinium bromide, 2-acetyl-1-methylpyridinium hydrogen sulfate, 2-acetyl-1-allylpyridinium-p-toluenesulfonate, 2-acetyl-1-(2-hydroxyethyl)pyridinium-p-toluenesulfonate, 2-acetyl-1-(2-oxopropyl)pyridinium-p-toluenesulfonate, and 2-acetyl-1-(2-methoxyethyl)pyridinium-p-toluenesulfonate.

Bleaching power intensifiers of the 3,4-dihydroisoquinoline type that are further preferred according to the present invention include N-methyl-3,4-dihydroisoquinolinium-p-toluenesulfonate, N-methyl-3,4-dihydroisoquinoliniumbenzenesulfonate, N-methyl-3,4-dihydroisoquinolinium hydrogen sulfate, N-allyl-3,4-dihydroisoquinolinium-p-toluenesulfonate, N-allyl-3,4-dihydroisoquinoliniumbenzenesulfonate, N-allyl-3,4-dihydroisoquinolinium bromide, N-allyl-3,4-dihydroisoquinolinium acetate, 3,4-dihydro-2-(3-hydroxy-propyl)isoquinolinium-p-toluenesulfonate, 3,4-dihydro-2-(3-hydroxypropyl)isoquinoliniumbenzenesulfonate, 3,4-dihydro-2-(3-hydroxypropyl)isoquinolinium bromide, 3,4-dihydro-2-(3-hydroxypropyl)isoquinolinium acetate, 3,4-dihydro-2-(2-hydroxyethyl)isoquinolinium-p-toluenesulfonate, 3,4-dihydro-2-(2-hydroxyethyl)isoquinoliniumbenzenesulfonate, 3,4-dihydro-2-(2-hydroxyethyl)isoquinolinium bromide, or 3,4-dihydro-2-(2-hydroxyethyl)isoquinolinium acetate.

The bleaching power intensifiers used with or instead of peroxo compounds are present in cosmetic agents according to the present invention in quantities preferably from 0.5 to 30 wt %, particularly 2 to 20 wt %, based on total weight of the ready-to-use agent.

To further enhance the lightening performance, at least one optionally hydrated $SiO_2$ compound can be added to the composition as a bleaching power intensifier. Although even small quantities of optionally hydrated $SiO_2$ compounds can increase lightening performance, it may be preferred to use the optionally hydrated $SiO_2$ compounds in quantities from 0.05 wt % to 15 wt %, preferably from 0.15 wt % to 10 wt %, and more preferably from 0.2 wt % to 5 wt %, based on the anhydrous composition according to the present invention. The quantitative indications reflect in each case the concentration of $SiO_2$ compounds (without their water component) in the agents.

The present invention is in general not limited with regard to the optionally hydrated $SiO_2$ compounds. Silicic acids, oligomers and polymers thereof, and salts thereof are preferred. Preferred salts are the alkali salts, particularly the potassium and sodium salts. The sodium salts are very particularly preferred.

Optionally hydrated $SiO_2$ compounds can be present in various forms. $SiO_2$ compounds used according to the present invention are preferably in the form of silica gels, or particularly preferably as water glass. These $SiO_2$ compounds can be present in part in aqueous solution.

Very particularly preferred according to the present invention are water glasses that are constituted from a silicate of the formula $(SiO_2)_n(Na_2O)_m(K_2O)_p$, where n is a positive rational number and m and p, mutually independently, are a positive rational number or 0, with the proviso that at least one of the parameters m or p is different from 0, and that the ratio between n and the sum of m and p is from 1:4 to 4:1.

Metasilicates in particular (which in accordance with the formula above are notable for a ratio between n and the sum of m and p that is less than or equal to 1, and can be construed as chain-like polymeric structures of the $[SiO_3]^{2-}$ anion) can be used with preference. Sodium metasilicate, of the formula $[NaSiO_3]_x$, is particularly preferred in this context.

In addition to components described by the empirical formula, water glasses can also contain further additives, for example, phosphates or magnesium salts, in small quantities.

Water glasses that are particularly preferred according to the present invention are marketed, inter alia, by the Henkel company under the designations Ferrosil® 119, Natronwasserglas 40/42, Portil® A, Portil® AW, and Portil® W, and by the Akzo company under the designation Britesil® C20.

The hair-bleaching preparation can additionally contain at least one polymer in order to improve its loading onto the foil. Useful polymers in this context are nonionic polymers, for example, vinylpyrrolidone/vinyl acrylate copolymers, polyvinylpyrrolidinone or vinylpyrrolidinone/vinyl acetate copolymers, zwitterionic and amphoteric polymers, for example acrylamidopropyltrimethylammonium chloride/acrylate copolymers, anionic polymers such as polyacrylic acids or crosslinked polyacrylic acids, natural thickening agents or those derived from natural thickening agents such as agar-agar, guar gum, alginic acid, xanthan gum, gum arabic, karaya gum, locust bean flour, linseed gums, dextrans, cellulose derivatives, starch fractions and derivatives such as amylose, amylopectin, and dextrins, or entirely synthetic hydrocolloids such as poly(vinylalcohol).

Water-soluble polymers are useful with particular advantage in this context. Hair-bleaching preparations of this kind are particularly effectively released from the foil by the wetness of the hair strands wrapped around them, and can thus be distributed particularly well between the hair fibers. This results in a uniform lightening result. Particularly suitable polymers include cellulose, cellulose ethers such as methyl cellulose, hydroxypropyl cellulose, carboxymethyl cellulose, polyelectrolytes such as alginic acid, xanthan gum, gum arabic, or modified natural thickening agents such as reaction products of guar gum with chloroacetic acid, with ethylene oxide, or with propylene oxide, or polyvinyl alcohol.

Undesired color shifts can occur upon decolorization of hair, particularly hair having a dark initial color. The reason for this is that the natural hair color is determined by melanins in the cortex of the hair fibers, actual hair color determined by the ratio of the two pigment classes (eumelanins having brownish-black tones, and pheomelanins with reddish-orange tones). Natural melanin dyes are destroyed by oxidative action in the hair-bleaching process, resulting in decolorizing of the fibers. Because of the differing oxidative destruction rates of the various classes of melanin pigment, hairs are not uniformly decolorized. In darker fibers having high melanin content, a certain proportion of dyes usually remains and is often expressed as yellowish to reddish shades. A color shift toward warm tones therefore occurs especially in the hair bleaching of darker hair.

Such color shifts toward warm tones are usually undesired by the user. This color shift is therefore usually counteracted by toning with the corresponding complementary color according to color theory. The objective here is a bleaching result giving a cool, silvery impression. The skilled artisan uses the term "frosting" in this connection. Depending on the initial hair color, an appropriate toning agent mixture must be used so that more-reddish color shifts are correspondingly compensated for with more-greenish toning agents, or more-yellowing color shifts with fairly violet toning agents.

Substantive dyes, particularly those that are sufficiently stable under the oxidizing and highly alkaline conditions of a hair-bleaching process, are suitable as toning agents.

In a further embodiment, the hair-bleaching preparation additionally contains a combination of at least one blue substantive dye and one red substantive dye, with the weight ratio between the sum of all blue substantive dyes and the sum of all red substantive dyes having a value greater than or equal to 1. It is thereby possible to avoid undesired color shifts toward pink/rosé shades.

In preferred agents according to the present invention the total weight of all blue substantive dyes is greater than the total weight of all red substantive dyes. Preferred agents are therefore characterized in that the weight ratio between the sum of all blue substantive dyes and the sum of all red substantive dyes is from 1 to 100, preferably from 1.5 to 10, and particularly preferably from 2 to 4.

In principle, there are no limits to the selection of the substantive dyes. Substantive dyes are usually subdivided into anionic, cationic, and nonionic substantive dyes. Useful substantive dyes include nitrophenylenediamines, nitroaminophenols, azo dyes, anthraquinones, or indophenols, if these substantive dyes possess sufficient stability with respect to the harsh conditions of the hair-bleaching process.

The agent preferably contains, as a blue substantive dye, at least one anionic substantive dye, particularly one selected from compounds having the designation "bromophenol blue" or "tetrabromophenol blue."

The agent preferably contains, as a red substantive dye, at least one anionic substantive dye, preferably from the group of fluorescein dyes. Particularly preferred red substantive dyes are known under the designations Acid Red 92, Acid Red 98, Acid Red 94, Acid Red 87, and Acid Red 51. Acid Red 92 (also D&C Red no. 28 or Phloxin B) is very particularly preferred.

Preferred dye combinations according to the present invention for frosting in the hair-bleaching preparation are those that having at least the combination of
tetrabromophenol blue and Acid Red 92,
tetrabromophenol blue and Acid Red 98,
tetrabromophenol blue and Acid Red 94,
tetrabromophenol blue and Acid Red 87, or
tetrabromophenol blue and Acid Red 51.

It may further be preferred if the hair-bleaching preparation contains further substantive dyes. In particular, the agent contains a yellow and/or orange dye as a further substantive dye. This is advantageous when undesired reddish color shifts occur in the hair-bleaching process.

Yellow dyes are preferably chosen from suitable yellow nitro dyes such as 1,2-diamino-4-nitrobenzene (C.I. 76,020), 1-[(2-hydroxyethyl)amino]-2-nitrobenzene (HC Yellow 2), 1-(2-hydroxyethoxy)-2-[(2-hydroxyethyl)amino]-5-nitrobenzene (HC Yellow 4), 1-amino-2-[(2-hydroxyethyl)amino]-5-nitrobenzene (HC Yellow 5), 4-[(2,3-dihydroxypropyl)amino]-3-nitro-1-trifluoromethylbenzene (HC Yellow 6), 2-[di(2-hydroxyethyl)amino]-5-nitrophenol, 2-[(2-hydroxyethyl)amino]-1-methoxy-5-nitrobenzene, 2-amino-3-nitrophenol, 2-amino-4-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 3-[(2-aminoethyl)amino]-1-methoxy-4-nitrobenzene hydrochloride (HC Yellow 9), 1-chloro-2,4-bis [(2-hydroxyethyl)amino]-5-nitrobenzene (HC Yellow 10), 2-[(2-hydroxyethyl)amino]-5-nitrophenol (HC Yellow 11), 1-[(2'-ureidoethyl)amino]-4-nitrobenzene, 1-amino-4-[(2-aminoethyl)amino]-5-methyl-2-nitrobenzene, 4-[(2-hydroxyethyl)amino]-3-nitro-1-methylbenzene, 1-chloro-4-[(2-hydroxyethyl)amino]-3-nitrobenzene (HC Yellow 12), 4-[(2-hydroxyethyl)amino]-3-nitro-1-trifluoromethylbenzene (HC Yellow 13), 4-[(2-hydroxyethyl)amino]-3-nitrobenzonitrile (HC Yellow 14), 4-[(2-hydroxyethyl)amino]-3-nitrobenzamide (HC Yellow 15) 3-[(2-hydroxyethyl)amino]-4-methyl-1-nitrobenzene, 4-chloro-3-[(2-hydroxyethyl)amino]-1-nitrobenzene. Suitable yellow or orange quinone dyes are, in particular, 2[(2-aminoethyl)

amino]-9,10-anthraquinone (HC Orange 5) and 2-hydroxy-1,4-naphthoquinone (C.I. 75,480, Natural Orange 6). Neutral yellow or orange azo dyes can also be used advantageously according to the present invention, in particular 4-[(4-aminophenyl)azo]-1-[di(2-hydroxyethyl)amino]-3-methylbenzene (HC Yellow 7), 2,6-diamino-3-[(pyridin-3-yl)azo]pyridine, 2-{[4-(acetylamino)phenyl]azo}-4-methylphenol (C.I. 11855; Disperse Yellow 3), 4-[(4-nitrophenyl)azo]aniline (C.I. 11,005; Disperse Orange 3). Particularly suitable as yellow or orange anionic substantive dyes are 6-hydroxy-5-[(4-sulfophenyl)azo]-2-naphthalenesulfonic acid disodium salt (C.I. 15,985; Food Yellow No. 3; FD&C Yellow No. 6), 2,4-dinitro-1-naphthol-7-sulfonic acid disodium salt (C.I. 10,316; Acid Yellow 1; Food Yellow No. 1), 2-(indane-1,3-dion-2-yl)quinoline-x,x-sulfonic acid (mixture of mono- and disulfonic acid) (C.I. 47,005; D&C Yellow No. 10; Food Yellow No. 13; Acid Yellow 3, Yellow 10), 4-((4-amino-3-sulfophenyl)azo)benzenesulfonic acid disodium salt (C.I. 13,015, Acid Yellow 9), 5-hydroxy-1-(4-sulfophenyl)-4-[(4-sulfophenyl)azo]pyrazole-3-carboxylic acid trisodium salt (C.I. 19,140; Food Yellow No. 4; Acid Yellow 23), 3-[(4-phenylamino)phenyl]azobenzenesulfonic acid sodium salt (C.I. 13,065; Ki406; Acid Yellow 36), 9-(2-carboxyphenyl)-6-hydroxy-3H-xanthen-3-one (C.I. 45,350; Acid Yellow 73; D&C Yellow No. 8), 5-[(2,4-dinitrophenyl)amino]-2-phenylaminobenzenesulfonic acid sodium salt (C.I. 10,385; Acid Orange 3), 4-[(2,4-dihydroxyphenyl)azo]benzenesulfonic acid sodium salt (C.I. 14,270; Acid Orange 6), 4-[(2-hydroxynaphth-1-yl)azo]benzenesulfonic acid sodium salt (C.I. 15,510; Acid Orange 7), 4-[(2,4-dihydroxy-3-[(2,4-dimethylphenyl)azo]phenyl)azo]benzenesulfonic acid sodium salt (C.I. 20,170; Acid Orange 24). Suitable cationic substantive dyes are in particular 3-[(4-amino-2,5-dimethoxyphenyl)azo]-N,N,N-trimethylbenzolaminium chloride (C.I. 12,605, Basic Orange 69), di[4-(dimethylamino)phenyl]iminomethane hydrochloride (C.I. 41,000; Basic Yellow 2), 2-[2-((2,4-dimethoxyphenyl)amino)ethenyl]-1,3,3-trimethyl-3H-indol-1-ium chloride (C.I. 48,055; Basic Yellow 11), 3-methyl-1-phenyl-4-[(3-(trimethylammonio)phenyl)azo]pyrazol-5-one chloride (C.I. 12,719; Basic Yellow 57). Preferred yellow or orange cationic substantive dyes are Basic Yellow 87 and Basic Orange 31. Particularly preferred yellow or orange nonionic substantive dyes are those known under the international designations resp. trade names HC Yellow 2, HC Yellow 4, HC Yellow 5, HC Yellow 6, HC Yellow 12, HC Yellow 13, HC Orange 1, and Disperse Orange 3, in particular HC Yellow 13.

Preferably the substantive dyes are present in the hair-bleaching preparation at a proportion of 0.0001 wt % to 5.0 wt %, particularly 0.001 wt % to 2.5 wt %, and very particularly preferably 0.01 wt % to 1.5 wt %, based on total weight of the ready-to-use agent.

It is furthermore proven advantageous if the hair-bleaching agent preparations contain at least one stabilizer or complexing agent. Particularly preferred stabilizers are phenacetin, alkali benzoates (sodium benzoate), and salicylic acid.

Also preferred according to the present invention is the use of complexing agents. Complexing agents are substances that can complex metal ions. Preferred complexing agents are chelate complexing agents that form bonds with a metal ion via multiple coordination sites.

All complexing agents of the existing art can be used in the context of the present invention. These can belong to different chemical groups. The following are preferably used, individually or in a mixture with one another:

a) polycarboxylic acids in which the sum of the carboxyl and (if applicable) hydroxyl groups equals at least 5, such as gluconic acid;
b) nitrogen-containing mono- or polycarboxylic acids such as ethylenediaminetetraacetic acid (EDTA), N-hydroxyethylethylenediaminetriacetic acid, diethylenetriaminepentaacetic acid (DTPA), ethylenediaminedisuccinic acid (EDDS), hydroxyethyliminodiacetic acid, nitridodiacetic acid-3-propionic acid, isoserinediacetic acid, N,N-di-(2-hydroxyethyl)glycine, N-(1,2-dicarboxy-2-hydroxyethyl)glycine, N-(1,2-dicarboxy-2-hydroxyethyl)aspartic acid or nitrilotriacetic acid (NTA), ethylenediaminediglutaric acid (EDGA), 2-hydroxypropylenediaminedisuccinic acid (HPDS), glycinamide-N,N'-disuccinic acid (GADS), ethylendiamine-N-N'-diglutaric acid (EDDG), 2-hydroxypropylenediamine-N-N'-disuccinic acid (HPDDS), diaminoalkyldi-(sulfosuccinic acid) (DDS), ethylenedicysteic acid (EDC), ethylenediamine-N-N'-bis(orthohydroxyphenyl)acetic acid (EDDHA), N-2-hydroxyethylamine-N,N-diacetic acid, glyceryliminodiacetic acid, iminodiacetic acid-N-2-hydroxypropylsulfonic acid, aspartic acid-N-carboxymethyl-N-2,5-hydroxypropyl-3-sulfonic acid, β-alanine-N,N'-diacetic acid, aspartic acid-N,N'-diacetic acid, aspartic acid-N-monoacetic acid, dipicolinic acid, as well as salts and/or derivatives thereof;
c) geminal diphosphonic acids such as 1-hydroxyethane-1,1-diphosphonic acid (HEDP), higher homologs thereof having up to 8 carbon atoms, and hydroxy- or amino-group-containing derivatives thereof, and 1-aminoethane-1,1-diphosphonic acid, higher homologs thereof having up to 8 carbon atoms, and hydroxy- or amino-group-containing derivatives thereof;
d) aminophosphonic acids such as ethylenediaminetetra(methylenephosphonic acid) (EDTMP), diethylenetriaminepenta(methylenephosphonic acid) (DTPMP) and higher homologs thereof, or nitrilotri(methylenephosphonic acid);
e) phosphonopolycarboxylic acids such as 2-phosphonobutane-1,2,4-tricarboxylic acid;
f) cyclodextrins; and
g) alkali stannates (sodium stannate), alkali pyrophosphates (tetrasodium pyrophosphate, disodium pyrophosphate), alkali phosphates (sodium phosphate), and phosphoric acid.

Preferred complexing agents include nitrogen-containing polycarboxylic acids, particularly EDTA, and phosphonates, preferably hydroxyalkane-resp. aminoalkanephosphonates, and in particular 1-hydroxyethane-1,1-diphosphonate (HEDP) resp. the di- or tetrasodium salt thereof, and/or ethylenediaminetetramethylenephosphonate (EDTMP) resp. the hexasodium salt thereof, and/or diethylenetriaminepentamethylenephosphonate (DTPMP) resp. the hepta- or octasodium salt thereof Preferred hair-bleaching agents for keratinic fibers possess an alkaline pH. In a further preferred embodiment the ready-to-use agent has a pH from 7.0 to 12.0, preferably from 8.0 to 11.0. The pH values for purposes of the present invention are pH values measured at a temperature of 22° C. The pH is usually adjusted using pH adjusting agents. The skilled artisan is familiar, for purposes of adjusting the pH, with acidifying and alkalizing agents common in cosmetics. Alkalizing agents usable for adjusting pH are typically chosen from inorganic salts, particularly alkali and alkaline-earth metals, organic alkalizing agents, in particularly amines, basic amino acids, and alkanolamines, and ammonia. Preferred acidifying agents include edible acids such as citric acid, acetic acid, malic acid, or tartaric acid, as well as dilute mineral acids.

It has been found that preferred hair-bleaching preparations additionally contain an inorganic solid alkalizing agent. This alkalizing agent goes at least partly into solution upon contact with the moisture of the hair strands, thereby establishing the alkaline pH necessary for hair-bleaching operations. The inorganic alkalizing agent according to the present invention is preferably chosen from sodium hydroxide, potassium hydroxide, calcium hydroxide, barium hydroxide, sodium phosphate, potassium phosphate, sodium silicate, potassium silicate, sodium carbonate, and potassium carbonate. Compositions according to the present invention contain alkalizing agents preferably in quantities from 0.2 to 25 wt %, particularly 0.5 to 10 wt %.

In one embodiment, the cosmetic hair-bleaching preparation accounts for at least 10 wt %, preferably at least 25 wt %, and particularly 50 wt % of the total weight of the foil.

For utilization, one or more applicator foils according to the present invention loaded with hair-bleaching preparation is wrapped around a wet bundle of keratinic fibers, for example, a wet strand of human hair. If necessary, the hair-bleaching preparation can also be additionally moistened with water directly before utilization.

A further subject of the present invention is therefore a method for lightening keratinic fibers wherein at least one wet bundle of the keratinic fibers is laid onto an applicator foil of the first subject of the invention and wrapped in the foil. The bundle of keratinic fibers is, in particular, a wet or moist strand of hair.

It can be immaterial in this context whether the hair strand has been separated from the wet hair and is still sufficiently moistened, or whether the hair strand has been isolated from the dry hair and moistened immediately before being wrapped in the applicator foil.

For lightening longer hair, it is useful to isolate a bundle of keratinic fibers or a strand from the hair that is still dry, to moisten the bundle resp. strand well, and to wrap the bundle, thereby moistened, in the applicator foils for lightening. A spray bottle is particularly suitable in this context for moistening the strand.

In a further embodiment of the method according to the present invention a strand of human hair, as a bundle of keratinic fibers, is isolated from the dry hair, thoroughly moistened with water on the applicator foil, and immediately thereafter wrapped in the foil.

Depending on the user's need and desire, individual or multiple different strands distributed over all of the hair can be wrapped in this manner. Single-point, grouped, or uniformly distributed accents and highlights can thereby be produced on the hair.

Depending on the lightening desired, strands wrapped in the applicator foil remain for a certain contact time at room temperature or at elevated temperature from 25 to 45° C. The contact time is from 1 to 60 minutes, preferably 5 to 45 minutes, and particularly 10 to 30 minutes. The foils are then removed and the strands rinsed with water or with a post-treatment preparation, such as a commercially available conditioner or shampoo, and dried.

In an embodiment of the method according to the present invention the foil is removed from the strand(s) after a contact time from 1 to 45 minutes, and the keratinic fibers rinsed out.

A further subject of the present invention is the use of at least one applicator foil of the first subject of the invention to generate selective, lightened highlights in human hair. Natural, attractive color accents and highlights can be achieved in this fashion, particularly for uniformly colored hair or a naturally very homogeneous hair color. With pronounced lightening, sharp contrasts and accented areas within hairstyle are thereby possible.

Use of these applicator foils in combination with or in close chronological succession after further coloring and shape-modifying agents, for example oxidizing lightening and/or coloring agents, is likewise possible, and can be applied accordingly by the skilled artisan or the user in accordance with his or her needs and desires.

Statements made regarding the applicator foils according to the present invention apply mutatis mutandis with respect to further preferred embodiments of the methods and uses according to the present invention.

We claim:

1. Method for lightening keratinic fibers comprising:
   laying at least one bundle of keratinic fibers onto a foil applicator, wherein the foil applicator comprises:
      a sheet-shaped substrate, and a cosmetic hair-bleaching preparation applied onto the substrate prior to laying the at least one bundle of keratinic fibers onto the foil applicator, wherein the cosmetic hair-bleaching preparation is anhydrous having a water content of less than 1.0 wt. % based on total weight of the cosmetic hair-bleaching preparation and comprises at least one solid peroxodisulfate salt and at least one solid addition product of hydrogen peroxide with organic or inorganic compounds, wherein the at least one solid addition product of hydrogen peroxide with organic or inorganic compounds is present in an amount of from 0.1 to 60 wt. % based on the total weight of the cosmetic hair-bleaching preparation, and wherein pre-mixing of the cosmetic hair-bleaching preparation on the foil applicator is eliminated;
   wrapping the keratinic fibers in the foil,
   leaving the keratinic fiber in the applicator foil for a contact time,
   removing the foil, and
   rinsing the keratinic fibers out.

2. Method according to claim 1 comprising isolating a strand of dry human hair as a bundle of keratinic fibers from dry hair, thoroughly moistening the strand with water on the foil applicator, and immediately thereafter wrapping the strand in the foil.

3. Method according to claim 1, wherein the contact time is from 1 to 45 minutes, and after the contact time, removing the foil from the strand and rinsing the keratinic fibers out.

4. Method according to claim 1, wherein the sheet-shaped substrate is fully covered with the cosmetic hair-bleaching preparation.

5. Method according to claim 1, wherein the cosmetic hair-bleaching preparation is applied only to specific areas of the substrate.

* * * * *